United States Patent [19]

Rosenthal

[11] Patent Number: 4,801,804

[45] Date of Patent: * Jan. 31, 1989

[54] METHOD AND APPARATUS FOR NEAR INFRARED REFLECTANCE MEASUREMENT OF NON-HOMOGENEOUS MATERIALS

[75] Inventor: Robert D. Rosenthal, Gaithersburg, Md.

[73] Assignee: Trebor Industries, Inc., Gaithersburg, Md.

[*] Notice: The portion of the term of this patent subsequent to Dec. 30, 2003 has been disclaimed.

[21] Appl. No.: 913,468

[22] Filed: Sep. 30, 1986

[51] Int. Cl.$^4$ .......................................... G01N 21/55
[52] U.S. Cl. ................................. 250/341; 250/252.1; 250/339; 250/358.1; 356/243; 356/446
[58] Field of Search ..................... 250/241, 358.1, 339, 250/252.1; 356/446, 243

[56] References Cited

U.S. PATENT DOCUMENTS

| | | | |
|---|---|---|---|
| 3,776,642 | 12/1973 | Anson | 356/188 |
| 4,029,420 | 6/1977 | Simms | 356/446 |
| 4,037,970 | 7/1977 | Webster et al. | 356/446 |
| 4,095,105 | 6/1978 | Rosenthal | 250/341 |
| 4,286,327 | 8/1981 | Rosenthal et al. | 364/498 |
| 4,379,233 | 4/1983 | Rosenthal | 250/553 |
| 4,404,642 | 9/1983 | Rosenthal | 364/571 |
| 4,484,819 | 11/1984 | Ulrich | 356/446 |
| 4,487,278 | 12/1984 | Rosenthal | 177/25 |
| 4,633,087 | 12/1986 | Rosenthal | 250/341 |

FOREIGN PATENT DOCUMENTS 823832 11/1959 United Kingdom ................ 356/243

OTHER PUBLICATIONS

Rosenthal, Robert D., "An Introduction to Near Infrared Quantitative Analysis," 1977 Annual Meeting of American Association of Cereal Chemists.

Primary Examiner—Carolyn E. Fields
Attorney, Agent, or Firm—Bernard, Rothwell & Brown

[57] ABSTRACT

A method and apparatus for near infrared reflectance measurement of non-homogeneous materials. Constituents of a material are quantitatively analyzed by reflectance techniques utilizing a planar surface of the material within a cup-shaped sample holder opaque to near-infrared radiation. A predetermined area of the planar surface is uniformly irradiated with near infrared radiation emitted from a source spaced a predetermined distance away from the planar surface. Near infrared radiation reflected by substantially all of the predetermined surface area is detected with a near infrared radiation detector spaced a predetermined distance away from the planar surface, to provide a signal which is processed to measure an average content of a constituent in the sample material. The source and detector are contained in a probe which is calibrated by inserting the probe into a cavity. The probe is spaced from the bottom of the cavity such that the cavity reflectance is about equal to that of the material for which the probe is being calibrated.

10 Claims, 3 Drawing Sheets

METHOD AND APPARATUS FOR NEAR INFRARED REFLECTANCE MEASUREMENT OF NON-HOMOGENEOUS MATERIALS

BACKGROUND OF THE INVENTION

1. Field of the Invention

This invention relates to improvements in methods and in apparatus for measurement of a constituent of a material utilizing near-infrared reflectance techniques.

2. Description of the Background Art

There is much prior art on the use of near-infrared radiation for the measurement of organic materials. Much of such art was pioneered by Robert D. Rosenthal and Trebor Industries, Inc. in their various instruments which provide near-infrared quantitative analysis. See, e.g. "An Introduction to Near Infrared Quantitative Analysis" presented by Robert Rosenthal from the 1977 Annual Meeting of American Association of Cereal Chemists, and Rosenthal U.S. Pat. Nos. 4,286,327, 4,404,642; 4,379,233; 4,487,278, all assigned to Trebor Industries, Inc. of Gaithersburg, Maryland.

Reflectance techniques have been used for analysis of components of grain, see for example, U.S. Pat. No. 3,776,642, Anson et al., assigned to Dickey-John Corporation which uses the near-infrared reflectance techniques and a rotating sample. The use of these near-infrared reflecance techniques requires the samples to be much more homogeneous than is possible with certain raw materials, e.g., ground sunflower seeds. Thus, large errors occur if conventional near-infrared reflectance measurement is attempted on ground sunflower seeds.

Nevertheless, there is a substantial need in the art to measure materials which are very non-homogeneous such as ground sunflower seeds. For example, ground sunflower seeds contain portions of the hull which differ greatly from the center portions of the hull seed, thus even the ground sunflower seed product is very non-homogeneous.

In the application of Rosenthal, et al., Ser. No. 726,658 filed Apr. 24, 1985, (now U.S. Pat. No. 4,633,087 issued Dec. 30, 1986) there is disclosed a means of measuring organic constituents in materials utilizing an interactance technique. In the application, the interactance technique utilizes a light beam source which must be in contact with the object being measured. A small amount of light that enters the object is scattered within the object and re-emits on the same side, but adjacent to the area of the object where the light contacted it. This interactance approach is best suited to materials which are pliable and at least moderately optically transmittive, for example, the human skin. This technique has also found application in a commercial machine for instantly analyzing the amount of fat in ground beef. Such machine is sold commercially under the trademark "The Lean Machine." However, until the present invention it was not possible to utilize the interactance tehniques of U.S. Pat. No. 4,633,087, for non-pliable materials or materials that have a high degree of opacity.

SUMMARY OF THE INVENTION

In accordance with the present invention, an apparatus for measuring a conttituent of a sample material comprises a sample holder having a chamber for containing a sample material having a constituent to be measured, the sample holder being formed of near infrared-opaque material. The apparatus includes means for forming a substantially planar surface of the sample material within the chamber, and a source of highly diffuse, near infrared radiation. The near infrared radiation source is spaced a predetermined distance away from the planar surface of the sample material so as to irradiate a predetermined surface area of the planar surface with substantially uniform, highly diffuse, near infrared radiation. A near infrared radiation detector is spaced a predetermined distance away from the planar surface of the sample material in position to detect near infrared radiation reflected by substantially all of the predetermined surface area. The predetermined surface area is sized to reflect near infrared radiation from the source to the detector which is indicative of an average content of the constituent of the sample material being measured. Near infrared radiation emitted from the source is prevented from directly impinging on the detector. The detector provides an electrical signal upon detection of near infrared radiation, and the electrical signal is processed to provide to measure an average content of the constituent of the sample material.

According to the method of this invention, a sample material having a constituent to be measured is provided within a near infrared-opaque chamber with the sample material having a substantially planar surface. A predetermined surface area of the planar surface of the sample material is uniformly irradiated with substantially uniform, highly diffuse, near infrared radiation emitted from a near infrared radiation source. The near infrared radiation source is spaced a predetermined distance away from the planar surface for uniformly irradiating the predetermined surface area. Near infrared radiation reflected by substantially all of the predetermined surface area is detected with a near infrared radiation detector. The near infrared radiation detector is spaced a predetermined distance away from the planar surface of the sample material to detect near infrared radiation reflected by substantially all of the predetermined surface area. The predetermined surface area is sized to reflect near infrared radiation from the source to the detector which is indicative of an average content of the constituent of the sample material. The detector provides an electrical signal upon detection of near infrared radiation, and is positioned to prevent near infrared radiation emitted from the source from directly impinging on the detector. The electrical signal provided by the detector is processed to measure an average content of the constituent for the sample material.

DETAILED DESCRIPTION OF THE PREFERRED EMBODIMENTS

It has been discovered that the "light pipe" illumination approach disclosed in U.S. Pat. No. 4,633,087, issued Dec. 30, 1986 (incorporated herein by reference) can be utilized to measure non-homogeneous materials, provided an unusual means of illuminating a non-homogeneous material by reflectance is incorporated. More particularly, the light pipe illuminating means of U.S. Pat. No. 4,633,087 can be used as a reflectance measuring instrument and the need for a pliable or homogeneous sample can be eliminated by the use of the unique sample holding method and apparatus of this invention.

Figure 1:
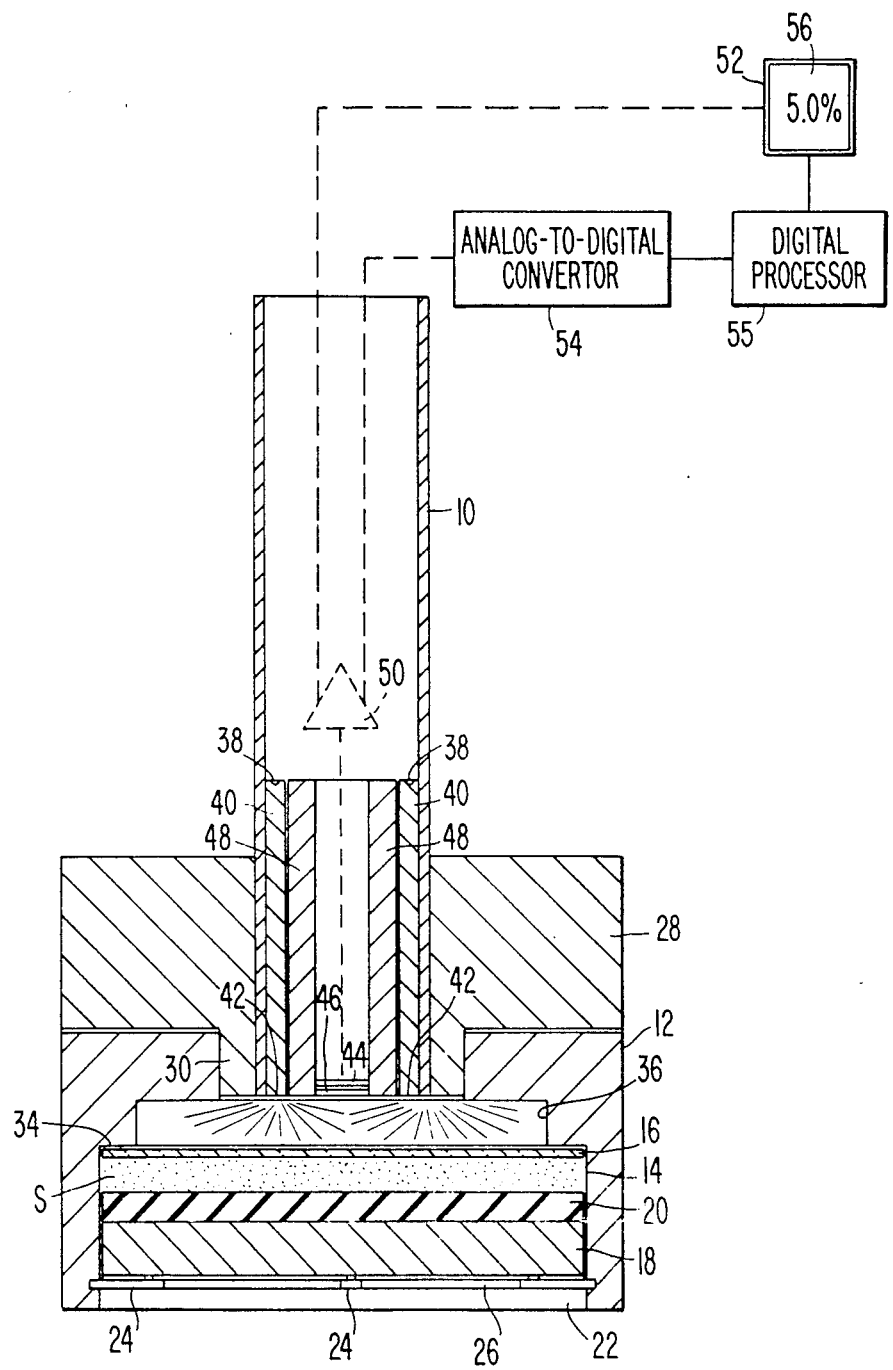
FIG. 1 is a cross-sectional view, partly schematic, of an apparatus according to the present invention.
Figure 2:
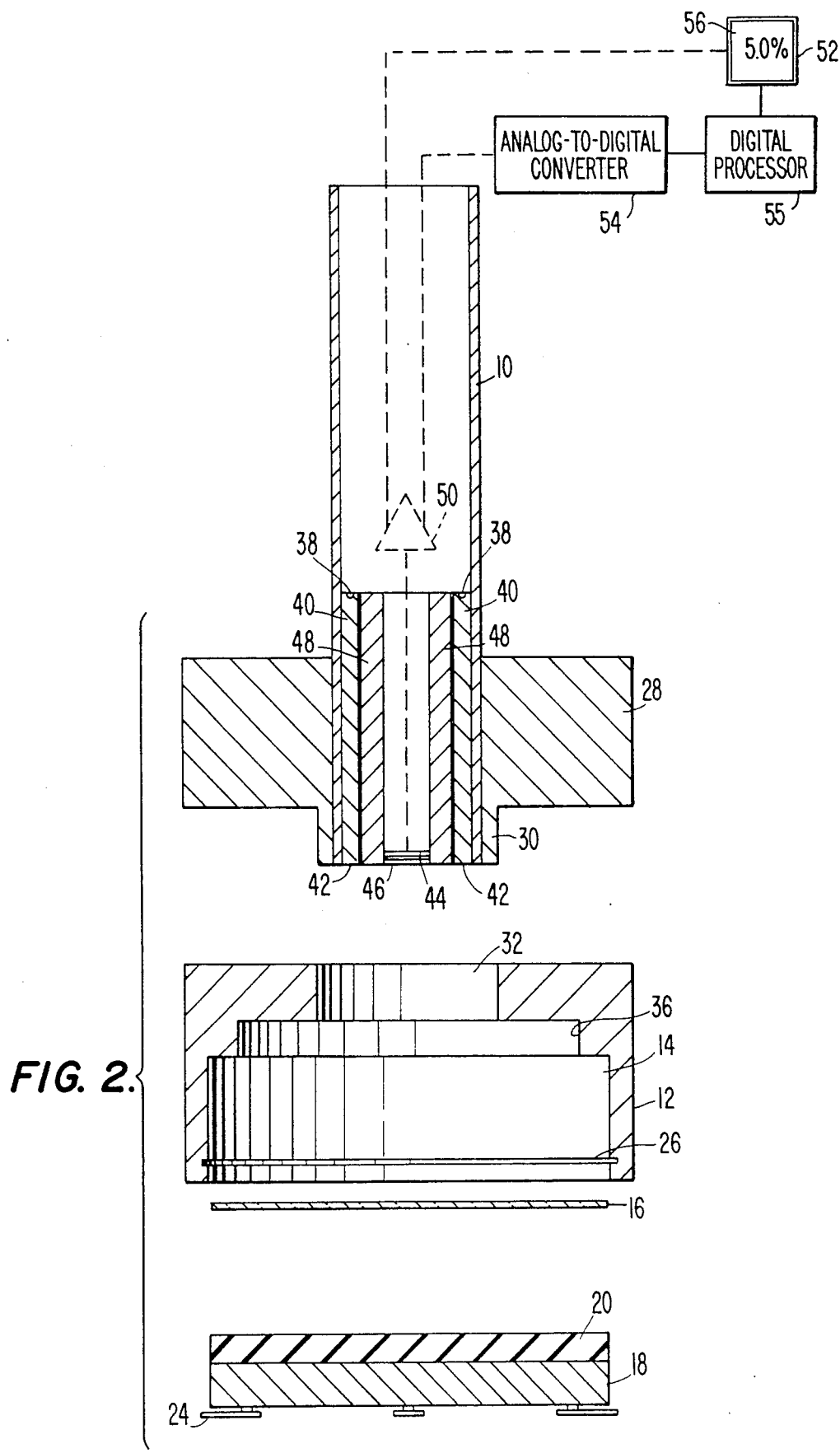
FIG. 2 is an exploded cross-sectional view of the apparatus shown in FIG. 1.

With reference to FIGS. 1 and 2, there is shown a probe 10 such as described in U.S. Pat. No. 4,633,087 to which further reference can be made for details of the probe not described herein.

The apparatus of the invention includes a sample holder 12 having a chamber 14 for containing a sample material having a constituent to be measured. The sample holder 12 is formed of near infrared-opaque material, and in the embodiment shown is cylindrical in shape.

Within the sample holder is a near infrared-transparent window 16 against which a substantially planar surface of the sample material S is formed within chamber 14.

In the preferred embodiment, the bottom of the chamber is closed by a removable disc 18 for admitting and withdrawing sample material from the chamber. Disc 18 is a "compression piston", the top portion of which is covered with a layer 20 of resilient material such as rubber for compressing the sample S against the window 16 at a substantially consistent packing density. Disc 18 complementarily fits within bottom opening 22 of sample holder 12 at relatively close tolerance to prevent ambient light from entering chamber 14 during measurement. During use, disc 18 is retained within the bottom opening of the sample holder by means of tabs 24 connected to disc 18 which can selectively be positioned within annular groove 26 in sample holder 12 for locking the disc in place.

In the embodiment shown, probe 10 is cylindrical and fits snugly within a complementary opening in a probe collar 28. Probe collar 28 may have an external diameter equivalent to that of sample holder 12, as shown. The probe collar includes a circular collar extension 30 which mates with a corresponding opening 32 in sample holder 12 with relatively close tolerance to prevent ambient light from entering the chamber 14 through opening 32 during use.

Probe 10 provides a source of highly diffuse, near infrared radiation, which is spaced a predetermined distance away from the planar surface 34 of sample S when probe collar 28 is joined with sample holder 12, so as to irradiate a predetermined surface area of planar surface 34 with substantially uniform, highly diffuse, near infrared radiation.

Probe 10 further includes a near infrared radiation detector which also is spaced a predetermined distance away from the planar surface 34 of sample S when collar 28 and sample holder 12 are joined such that the radiation detector is in position to detect near infrared radiation reflected by substantially all of the predetermined surface area of the sample material.

The predetermined surface area of the sample material 34 is framed by a cylindrical wall 36 above window 16 in sample holder 12. The predetermined surface area of sample S determined by wall 36 is of a size to reflect near infrared radiation from the end 42 of tube 40 to detector 44 which is indicative of an average content of a constituent being measured for the sample material S. The height of wall 36 thus provides detector 44 with a "view angle" of the entire predetermined surface area of sample S framed by wall 36. The surface area of sample S framed by wall 36 is sufficiently large to obtain an accurate percent content of the constituent being measured. The minimum size of the predetermined surface area framed by wall 36 will vary depending on the sample material being tested and its homogeneity, the less homogenous the material being tested, the larger the minimum predetermined surface area necessary for accurately obtaining an average content of the constituent being measured.

In the embodiment shown, and as described in greater detail in U.S. Pat. No. 4,633,087 the near infrared radiation source includes near infrared emitting diodes 38, each diode providing a point source of near infrared radiation.

Diodes 38 are positioned at one end of a tube 40 having a wall portion formed of a material which is capable of transmitting near infrared radiation but which does not substantially or inconsistently absorb near infrared radiation. Diodes 38 transmit near infrared radiation through the wall portion of tube 40. Tube 40 is of a sufficient length such that near infrared radiation from diodes 38 emerges substantially uniformly at an opposite end 42 of tube 40. End 42 of tube 40 emits the highly diffuse, near infrared radiation for irradiating the predetermined surface area of sample S framed by wall 36.

Within the bottom portion 42 of tube 40 is positioned a near infrared radiation detector 44. Protecting near infrared radiation detector 44 is an electro-magnetic interference shield comprised of a grounded, electrically conductive window 46 which is substantially transparent to near infrared energy.

A cylindrical, near infrared opaque shield 48 is positioned between detector 44 and tube 40 to prevent near infrared radiation emitted from tube 40 from impinging directly on detector 44.

Upon detection of near infrared radiation reflected from the planar surface of sample S, detector 44 generates an electrical signal indicative of the average content of the constituent being measured.

The electrical signal provided by detector 44 is processed through amplification of the signal by amplifier 50, which feeds the amplified signal to a readout box 52 which may have a display 56 for directly reading the percentage of a constituent such as oil and sample material S.

As described in U.S. Pat. No. 4,633,087, multiple readings can be taken to lower the noise utilizing data processing means. Multiple readings are accomplished by feeding the output of amplifier 50 to an integrating analog-to-digital converter 54 having a 12-bit output, which is connected to a digital processor 55 connected to readout box 52.

Figure 4:
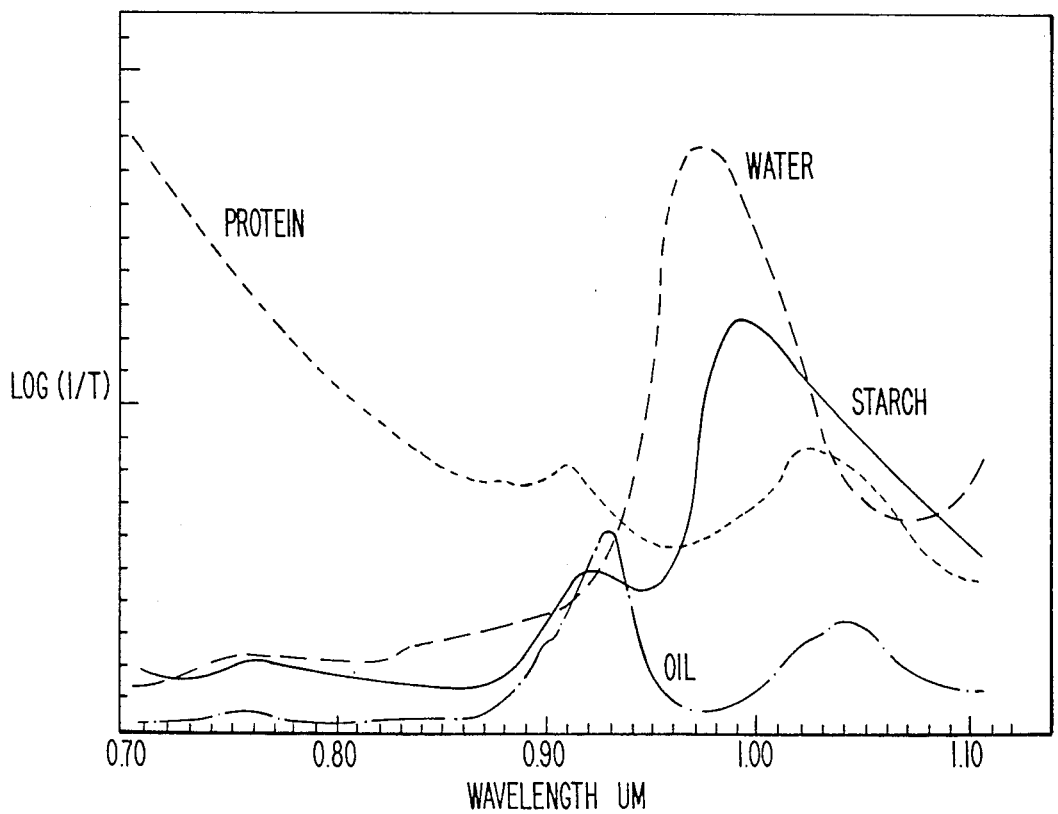
FIG. 4 is a graphic depiction of near infrared absorption spectra.

According to one embodiment for measuring fat/oil content of materials such as ground sunflower seeds, several pairs of infrared emitting diodes 38 are evenly spaced about the top of tube 40, such as three pairs of diodes spaced 180° apart. Two of the three diode pairs are selected within manufacturing tolerance to emit radiation with a peak wavelength of between 930 and 950 nanometers spaced 5 to 15 nanometers apart, thus corresponding to the oil/fat absorption shown in FIG. 4. The third pair of diodes are selected to emit radiation with a peak wavelength between 880 and 890 nanometers. An instrument according to this invention may be utilized to measure constituents other than oil/fat, such as starch, sugar, fiber, possibly protein and even moisture content. However, diodes that provide different wavelengths are used for these measurements (see FIG. 4). The present invention is also suitable for measuring paste-like samples.

For testing a variety of materials having different homogeneity characteristics using a single sample holder, it is advantageous to have a surface area framed by wall 36 which is larger than the minimum predetermined surface area necessary for accurate measurement of constituents of the various materials being tested. For example, a sample holder as shown is FIGS. 1 and 2 is suitable for the measurement of the fat/oil content of ground sunflower seeds and like materials. In the embodiment shown, the sample holder includes a cylindrically shaped wall 36 with a diameter of about 2½ inches and a height of about ¼ inch. When used with, a light probe as illustrated and described in U.S. Pat. No. 4,633,087, having about a one-inch outer diameter light tube 40 with a wall thickness of about ⅛ inch, quite accurate measurements of the fat/oil content of ground sunflower seeds and similar non-homogeneous materials are possible.

Figure 3:
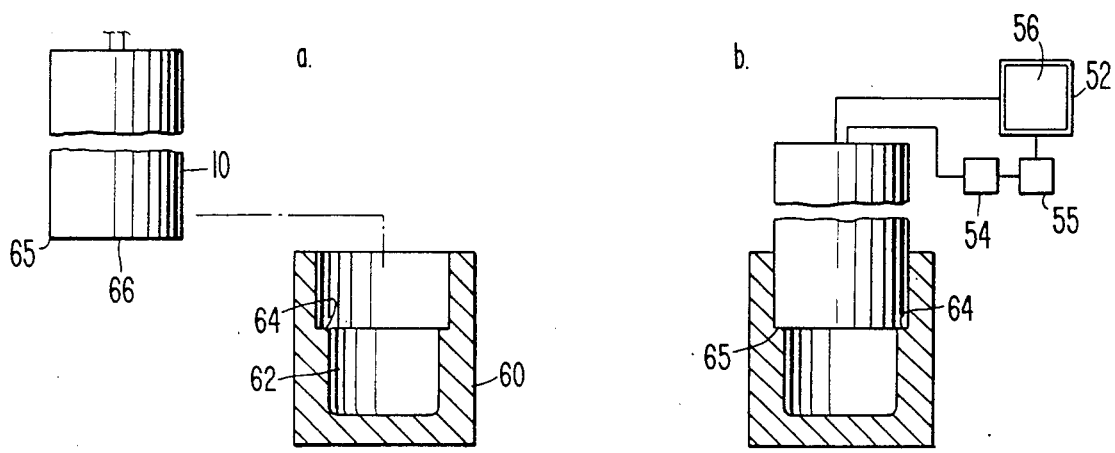
FIG. 3 is a schematic view in a step-by-step method employing a calibration cup in accordance with the invention.

FIG. 3 illustrates the use of a reflectance standard for calibrating the light probe. This reflectance standard is a cup 60 having a cavity 62 and an internal flange 64 for cooperating with the end 65 of probe 10. The dimensions are chosen such that the tip 66 of light probe 10 will be a predetermined distance from the bottom of cavity 62. This distance is chosen to provide a reflectance value approximately equal to the commodity being measured (which is a function of the material's reflection properties and the geometry of the cavity). The probe is calibrated by inserting the probe into the calibration chamber such that the tip 66 of the probe is spaced away from the bottom portion of cavity 62 so as to reflect sufficient near infrared radiation emitted from the top 66 back to the detector for calibrating the probe. The calibration cup is also directly usable for calibrating the probe for interactance measurements as in U.S. Pat. No. 4,633,087 as well as for reflectance measurements using the apparatus and method taught in this application. The material of the probe is chosen so that the reflectance characteristics makes it a usable standard for the constituent being measured, such as using polyvinyl chloride (PVC) for the calibration cup as a standard for fat/oil and other types of measurements.

A probe can be standardized according to the invention without the above-described calibration cup by placing a ceramic tile (or other optically consistent surface) within the sample holder illustrated in FIGS. 1 and 2 in place of sample material S.

It can be seen that this invention provides a significant advance in the art of measuring non-homogeneous materials utilizing near infrared radiation reflectance techniques by providing a non-homogeneous sample with it surface in a single plane within an opaque cavity spaced a predetermined distance from an interactance measuring probe.

Since many modifications, variations and changes in detail may be made to the described embodiment, it is intended that all matter in the foregoing description and shown in the accompanying drawings be interpreted as illustrative and not in a limiting sense.

What is claimed is:

1. A method for near infrared reflectance measurement of a constituent of a sample material utilizing a near infrared interactance quantitative analysis device, comprising:

(a) providing sample material having a constituent to be measured within a near infrared-opaque cahbmer with the sample material having a substantially planar surface;

(b) uniformly irradiating a pedetermined surface area of the planar surface of the sample material with substantially uniform, highly diffuse, multiple-wavelength near infrared radiation for uqantitative measurement of a sample constituent, which radiation is emitted from a multiple- wavelength near infrared radiation source spaced a predetermined distance away from the planar surface for uniformly irradiating said predetermined surface area;

(c) detecting near infrared radiation reflected by substantially all of said predetermined surface area with a near infrared radiation detector spaced a predetermined distance away from the planar surface of the sample material to detect near infrared radiation reflected by substantially all of said predetermined surface area, the predetermined surface area being sized to reflect near infrared radiaion from said source to said detector which is indicative of an average content of said consituent of said sample material, said detector providing an electrical signal upon detection of near infrared radiation, said detector being positioned so as to prevent near infrared radiation emitted from said source from directly impinging on said detector; and (d) processing an electrical signal provided by said detector to quantitatively measure an average content of said constituent for said sample material.

2. The method of claim 1 wherei nsaid soure nad said detector are parts of a probe, said method further comprising placing said probe in a complementary access opening in said chamber to position said source and said detector at said predetermined distance away form said planar surface of said smaple material for measuring said constituent of said sample material while preventing ambient light from reaching the sample during measurement.

3. The method of claim 2 further comprising calibrating said probe by inserting said probe into a calibration chamber having a cavity with a bottom portion having a predetermined geometrical shape spaced away from said source and said detector so as to reflect sufficient near infrared radiation emitted from said source to said detector for calibrating said probe.

4. An apparatus fro measuring a constituent of a sample material, comprising:

(a) a sample holder having a chamber for containing a sample material having a cosntituent to be measured, the sample holder being formed of near infrared-opaque material;

(b) means for forming a substantially planar surface of the sample material within the chamber;

(c) a source of highly diffuse, multiple-wavelength near infrared radiation for quantitative measurement of a sample constituent, said source being spaced a predetermined distance away from the planar surface of the sample material so as to irradiate a predetermined surface area of the planar surface with substantially uniform, highly diffuse, multiple-wavelength near infrared radiation;

(d) a near infrared radiation detector spaced a predetermined distance away from the planar surface of the sample material in position to detect near infrared radiation reflected by substantially all of said predetermined surface area, said predetermined surface area being sized to reflect near infrared radiation from said source to said detector which is indicative of an average content of said constituent of said sample material, said detector providing an electrical signal upon detction of near infrared radiation;

(e) means for preventing near infrared radiation emitted from said source from directly impinging on said detector;

(f) means for processing an electrical signal provided by said detector to quantitiatively measure an average content of said constituent for said sample material.

5. The apparatus of claim 4 wherein said source and said detector are parts of a probe comprising means for providing at least one point source of near infrared radiation; and a tube having a wall portion, the wall portion comprising a material which is capable of transmitting near infrared radiation; the material having a composition which does not substantially or inconsistently absorb near infrared radiation, the tube having first and second ends, the point source means being positioned at the first end of said tube for transmitting near infrared radiation through the wall portion of said tube, the tube being of a sufficient length that near infrared radiation from the point source means positioned at the first end of the tube will emerge substantially uniform at the second end of the tube; the second end of the tube emitting said highly diffuse near infrared radiation for irradiating said predetermined surface area; the second end of the tube peripherally defining a generally central area within which said near infrared radiation detector is positioned for detecting near infrared radiation entering the generally central area peripherally defined by the second end of the tube; said probe including said means for preventing near infrared radiation emitted from said source from directly impinging on said detector; said probe further comprising means for shielding the outside of the tube from ambient light; said probe mating with a complementary access opening in said chamber, for measuring said constituent of said sample material while preventing ambient light from reaching the sample during measurement.

6. The apparatus of claim 4 wherein the planar surface forming means comprises a near infrared-transparent window against which the planar surface is formed.

7. The apparatus of claim 6 further including means for compressing the sample against the window at substantially consistent packing density.

8. The apparatus of claim 7 wherein said sample holder incudes a removable bottom for admitting and withdrawing said sample material from said chamber, said bottom including said means for compressing the sample.

9. An apparatus for calibrating a probe for near infrared quantitative analysis, the calibrating apparatus comprising; a near infrared-opaque body, means defining a cavity in the body having a bottom portion with a predetermined geometrical shape, and means for positioning a light probe having a near infrared source and detector within the cavity of the body with the bottom portion of the cavity spaced away from said source and said detector a distance that provides the bottom portion of the cavity with a reflectane value that is about equal to the reflectance value of a material for which the probe is being calibrated, so as to reflect sufficient near infrared radiation emitted from said source to said detector for calibrating the probe.

10. A method for calibrating a prbe for near infrared quantitative analysis of a material, comprising:

(a) providing a near infrared-opaque body having a cavity therein with a bottom portion having a predetermined geometerical shape;

(b) positioning a light probe, having a near infrared source and detector, within the cavity of the body with the bottom portion of the cavity spaced away from said source and said detector a distance that provides the bottom portion of the cavity with a reflectance value that is about equal to the reflectance value of a material for which the probe is being calibrated, so as to reflect sufficient near infrared radiation emitted from such source to said detector for calibrating the probe; and (c) calibrating the probe while positioned as in step (b).

* * * * *